(12) United States Patent
Domansky et al.

(10) Patent No.: US 8,318,479 B2
(45) Date of Patent: Nov. 27, 2012

(54) PERFUSED THREE-DIMENSIONAL CELL/TISSUE DISEASE MODELS

(75) Inventors: Karel Domansky, Cambridge, MA (US); Linda G. Griffith, Cambridge, MA (US); Steven R. Tannenbaum, Framingham, MA (US); Alan Wells, Pittsburgh, PA (US); Samuel Walker Inman, Boston, MA (US)

(73) Assignees: Massachusetts Institute of Technology, Cambridge, MA (US); Univeristy of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 885 days.

(21) Appl. No.: 11/133,092

(22) Filed: May 19, 2005

(65) Prior Publication Data
US 2005/0260745 A1 Nov. 24, 2005

Related U.S. Application Data

(60) Provisional application No. 60/572,583, filed on May 19, 2004.

(51) Int. Cl.
*C12M 1/22* (2006.01)
*C12M 3/00* (2006.01)
*C12M 1/34* (2006.01)

(52) U.S. Cl. ............... 435/305.2; 435/384.1; 435/287.3; 435/288.2; 435/288.3; 435/288.5; 435/293.1; 435/305.1; 435/299.1; 435/307.1

(58) Field of Classification Search ............... 435/284.1, 435/287.3, 288.2, 288.3, 288.5, 293.1, 305.1, 435/305.2, 305.3, 307.1, 299.1
See application file for complete search history.

(56) References Cited

U.S. PATENT DOCUMENTS

| | | | |
|---|---|---|---|
| 4,033,825 A | 7/1977 | Haddad et al. |
| 4,060,081 A | 11/1977 | Yannas et al. |
| 4,485,096 A | 11/1984 | Bell |
| 4,485,097 A | 11/1984 | Bell |
| 4,520,821 A | 6/1985 | Schmidt et al. |
| 4,539,716 A | 9/1985 | Bell |
| 4,546,500 A | 10/1985 | Bell |

(Continued)

FOREIGN PATENT DOCUMENTS

EP 0 363 262 4/1990

(Continued)

OTHER PUBLICATIONS

Arias, et al., eds., *The Liver: Biology and Pathobiology*, Raven Press: New York, NY, 1988.

(Continued)

*Primary Examiner* — Nathan Bowers
(74) *Attorney, Agent, or Firm* — Pabst Patent Group LLP

(57) ABSTRACT

A system has been constructed that recapitulate the features of a capillary bed through normal human tissue. The system facilitates perfusion of three-dimensional (3D) cell monocultures and heterotypic cell co-cultures at the length scale of the capillary bed. A major feature is that the system can be utilized within a "multiwell plate" format amenable to high-throughput assays compatible with the type of robotics commonly used in pharmaceutical development. The system provides a means to conduct assays for toxicology and metabolism and as a model for human diseases such as hepatic diseases, including hepatitis, exposure-related pathologies, and cancer. Cancer applications include primary liver cancer as well as metastases. The system can also be used as a means of testing gene therapy approaches for treating disease and inborn genetic defects.

25 Claims, 2 Drawing Sheets

EXPLODED VIEW (TOP)

U.S. PATENT DOCUMENTS

| | | | |
|---|---|---|---|
| 4,729,949 A | 3/1988 | Weinreb et al. | |
| 4,734,372 A | 3/1988 | Rotman | |
| 4,894,343 A | 1/1990 | Tanaka et al. | |
| 5,010,014 A | 4/1991 | Gebhardt | |
| 5,153,132 A | 10/1992 | Goodwin et al. | |
| 5,169,601 A | 12/1992 | Ohta et al. | |
| 5,190,878 A | 3/1993 | Wilhelm et al. | |
| 5,204,055 A | 4/1993 | Sachs et al. | |
| 5,424,209 A | 6/1995 | Kearney | |
| 5,443,950 A | 8/1995 | Naughton et al. | |
| 5,451,524 A | 9/1995 | Coble et al. | |
| 5,459,069 A | 10/1995 | Palsson et al. | |
| 5,510,254 A | 4/1996 | Naughton et al. | |
| 5,512,474 A | 4/1996 | Clapper et al. | |
| 5,518,680 A | 5/1996 | Cima et al. | |
| 5,559,022 A | 9/1996 | Naughton et al. | |
| 5,595,909 A | 1/1997 | Hu et al. | |
| 5,599,788 A | 2/1997 | Purchio et al. | |
| 5,602,026 A | 2/1997 | Dunn et al. | |
| 5,602,028 A | 2/1997 | Minchinton | |
| 5,602,029 A | 2/1997 | Miyamoto | |
| 5,605,835 A | 2/1997 | Hu et al. | |
| 5,612,188 A | 3/1997 | Shuler et al. | |
| 5,624,840 A | 4/1997 | Naughton et al. | |
| 5,650,323 A | 7/1997 | Root | |
| 5,658,797 A | 8/1997 | Bader | |
| 5,674,742 A | 10/1997 | Northrup et al. | |
| 5,700,688 A | 12/1997 | Lee et al. | |
| 5,843,767 A | 12/1998 | Beattie | |
| 6,015,674 A | 1/2000 | Woudenberg et al. | |
| 6,037,171 A | 3/2000 | Larsson | |
| 6,197,575 B1 | 3/2001 | Griffith et al. | |
| 6,548,263 B1* | 4/2003 | Kapur et al. | 506/32 |
| 7,374,906 B2* | 5/2008 | Kirk et al. | 435/34 |
| 7,413,712 B2* | 8/2008 | Liu et al. | 422/100 |
| 7,445,926 B2 | 11/2008 | Mathies | |
| 2002/0028504 A1 | 3/2002 | MacCaskill et al. | |
| 2002/0173033 A1 | 11/2002 | Hammerick et al. | |
| 2003/0215941 A1* | 11/2003 | Campbell et al. | 435/325 |
| 2006/0110822 A1* | 5/2006 | Robbins et al. | 435/289.1 |
| 2006/0166357 A1* | 7/2006 | Takayama et al. | 435/289.1 |

FOREIGN PATENT DOCUMENTS

| | | |
|---|---|---|
| EP | 0 455 508 | 6/1991 |
| EP | 0 539 888 | 5/1993 |
| EP | 0 870 823 | 10/1998 |
| JP | 04262780 | 9/1992 |
| JP | 04278080 | 10/1992 |
| JP | 8154663 | 6/1996 |
| WO | WO 90/04645 | 5/1990 |
| WO | WO 95/24464 | 9/1995 |
| WO | WO 96/34087 | 10/1996 |
| WO | WO 96/40002 | 12/1996 |
| WO | WO 97/15394 | 5/1997 |

OTHER PUBLICATIONS

Bain, et al., "Embryonic stem cells express neuronal properties in vitro," Dev. Biol., 168:342-57 (1995).

Block, et al., "Population expansion, clonal growth, and specific differentiation patterns in primary cultures of hepatocytes induced by HGF/SF, EGF and TGF alpha in a chemically defined (HGM) medium," J. Cell Biol., 132:1133-49 (1996).

Cima, et al., "Tissue engineering by cell transplantation using degradable polymer substrates", J Biomech Eng., 113(2):143-51 (1991).

Cima, et al., "Hepatocyte culture on biodegradable polymeric substrates", Biotech. Bioeng., 38:145-58 (1991).

Cima, et al., "A theoretical and experimental evaluation of a novel radial-flow hollow fiber reactor for mammalian cell culture", Bioprocess Eng, 5:145-58 (1990).

Denk, et al., "Two-photon laser scanning fluorescence microscopy," Science, 248:73-76 (1990).

Dhadwal, et al., "Effects of anatomic variability on blood flow and pressure gradients in the pulmonary capillaries", J Appl Physiol., 83(5):1711-20 (1997).

Dimilla, et al., "Maximal migration of human smooth muscle cells on fibronectin and type IV collagen occurs at an intermediate attachment strength", J Cell Biol., 122(3):729-37 (1993).

Doetschman, et al. "The in vitro development of blastocyst-derived embryonic stem cell lines: formation of visceral yolk sac, blood islands and myocardium", J Embryol Exp Morphol., 87:27-45 (1985).

Doktycz, et al., "Genosensors and model hybridization studies" in Automation Technologies for Genome Characterization, T.J Beugelsdijk, ed. John Wiley and Sons, New York 1997).

Duffy, et al., "Rapid prototyping of microfluidic systems on poly(dimethylsiloxane)," Anal. Chem., 70: 4973-4984 (1998).

Encke, et al., "Genetic immunization generates cellular and humoral immune responses against the nonstructural proteins of the hepatitis C virus in a murine model", J Immunol., 161(9):4917-23 (1998).

Fontaine, et al., "Human hepatocyte isolation and transplantation into an athymic rat, using prevascularized cell polymer constructs," J. Ped. Surg., 30:56-60 (1995).

Geissler, et al., "Enhancement of cellular and humoral immune responses to hepatitis C virus core protein using DNA-based vaccines augmented with cytokine-expressing plasmids", J. Immunol., 158(3):1231-7 (1997).

Gendron, et al., "Induction of embryonic vasculogenesis by bFGF and LIF in vitro and in vivo," Dev. Biol., 177:332-46 (1996).

Griffith, et al., "In vitro organogenesis of liver tissue," Ann. N.Y. Acad., Sci., 831: 382-97 (1997).

Grover, et al., "Monolithic membrane valves and diaphragm pumps for practical large-scale integration into glass microfluidic devices," Sensors and Actuators, B 89:315-323 (2003).

Ingber, et al., "Mechanochemical switching between growth and differentiation during fibroblast growth factor-stimulated angiogenesis in vitro: role of extracellular matrix", J Cell Biol., 109(1):317-30 (1989).

Irvine, et al., "Comparison of tethered star and linear poly(ethylene oxide) for control of biomaterials surface properties", J Biomed Mater Res., 40(3):498-509 (1998).

Irvine, et al., "Self-consistent field analysis of grafted star polymers", Macromolecules, 29:6037-43 (1996).

Kennedy, et al., "A common precursor for primitive erythropoiesis and definitive haematopoiesis", Nature, 386(6624):488-93 (1997).

Kuhl and Griffith-Cima, "Tethered epidermal growth factor as a paradigm for growth factor-induced stimulation from the solid phase", Nat Med, 2(9):1022-7 (1996).

Lautt, et al., "Hepatic circulation and toxicology", Drug Metab Rev, 29(1-2):369-95 (1997).

Lee and Laibinis, "Protein-resistant coatings for glass and metal oxide surfaces derived from oligo(ethylene glycol)-terminated alkyltrichlorosilanes", Biomaterials, 19(18):1669-75 (1998).

Lee, et al., Protein-resistant surfaces prepared by Peo-containing block copolymer surfactants, J Biomed Mater Res., 23(3):351-68 (1998).

Li, et al., "Characterization of a 120-Kilodalton pre-S-binding protein as a candidate duck hepatitis B virus receptor", J Virol., 70(9):6029-35 (1996).

Liang, et al., "Rapid identification of low level hepatitis B-related viral genome in serum", J Clin Invest., 84(4):1367-71 (1989).

Lo, et al., "Fabrication of controlled release biodegradable foams by phase separation", Tissue Engineering, 1:15-28 (1995).

Masters, et al., "Multiphoton excitation fluorescence microscopy and spectroscopy of in vivo human skin", Biophys J. 72:2405-12 (1996).

Melegari, et al., "The small envelope protein is required for secretion of a naturally occurring hepatitis B virus mutant with pre-S1 deleted", J Virol., 71(7):5449-54 (1997).

Mikos, et al., "Laminated three-dimensional biodegradable foams for use in tissue engineering," Biomaterials, 14:323-330 (1993).

Mikos, et al., "Preparation of poly(glycolic acid) bonded fiber structures for cell attachment and transplantation," J. Biomed. Mater. Res., 27:183-189 (1993).

Millauer, et al., "High affinity VEGF binding and developmental expression suggest Flk-1 as a major regulator of vasculogenesis and angiogenesis," Cell, 72:835-46 (1993).

Mooney, et al., "Novel approach to fabricate porous sponges of poly(D,L-lactic-co-glycolic acid) without the use of organic solvents," *Biomaterials*, 17:1417-1422 (1996).

Mooney, et al., "Switching from differentiation to growth in hepatocytes: control by extracellular matrix", *J Cell Physiol.*, 151(3):497-505 (1992).

Moradpour, et al., "Specific targeting of human hepatocellular carcinoma cells by immunoliposomes in vitro", *Hepatology*, 22(5):1527-37 (1995).

Moradpour, et al., "Understanding hepatitis B virus infection", *N Engl J Med.*, 332(16):1092-3 (1995).

Powers, et al., "A microfabricated array bioreactor for perfused 3D liver culture," *Biotechnology and Bioengineering*, 78:257-69 (2002).

Powers, et al., "Cell-substratum adhesion strength as a determinant of hepatocyte aggregate morphology", *Biotech. Bioeng.*, 53:415-26 (1997).

Reddy, et al., "Proliferative response of fibroblasts expressing internalization-deficient epidermal growth factor (EGF) receptors is altered via differential EGF depletion effect," *Biotechnol. Prog.*, 10:377-84 (1994).

Sachs, et al., "CAD-casting: direct fabrication of ceramic shells and cores by three dimensional printing", *Manufacturing Review*, 5(2):117-26 (1992).

Saito, et al., "Molecular cloning of a murine IL-6 receptor-associated signal transducer, gp130, and its regulated expression in vivo," *J. Immunol.*, 148:4066-71 (1992).

Scaglioni, et al., "Posttranscriptional regulation of hepatitis B virus replication by the precore protein", *J Virol.*, 71(1):345-53 (1997).

Steinberg, et al., "Experimental specification of cell sorting, tissue spreading, and specific spatial patterning by quantitative differences in cadherin expression" *Proc Natl Acad Sci U S A.*, 91(1):206-9 (1994).

Tatarowicz, et al., "Repression of the HSV-1 latency-associated transcript (LAT) promoter by the early growth response (EGR) proteins: involvement of a binding site immediately downstream of the TATA box", *J Neurovirol.*, 3(3):212-24 (1997).

Tesh, et al., "The pathogenic mechanisms of Shiga toxin and the Shiga-like toxins," *Mol. Microbiol.*, 5:1817-22 (1991).

Thorsen, et al., "Microfluidic large-scale integration," *Science*, 298(5593):580-4 (2002).

Unger, et al., "Monolithic microfabricated valves and pumps by multilayer soft lithography," *Science*, 288(5463):113-6 (2000).

Vacanti, et al., "Tissue engineered growth of new cartilage in the shape of a human ear using synthetic polymers seeded with chondrocytes", *MRS Proceedings*, 252 (1992).

Vacanti, et al., "Beyond transplantation. Third annual Samuel Jason Mixter lecture," *Arch. Surg.*, 123:545-49 (1988).

Wakita, et al., "Specific inhibition of hepatitis C virus expression by antisense oligodeoxynucleotides. In vitro model for selection of target sequence", *J Biol Chem.*, 269(19):14205-10 (1994).

Wallis and Pomerantz, "Field assisted glass-metal sealing", *J. Appl. Physics*, 40:3946-49 (1969).

Walton, et al., "Creation of stable poly(ethylene oxide) surfaces on poly(methyl methacrylate) using blends of branched and linear polymers", *Macromolecules*, 30:6947-56 (1997).

Williams, et al., "Myeloid leukaemia inhibitory factor maintains the developmental potential of embryonic stem cells," *Nature*, 336:684-87 (1988).

Yoo, et al., "Regulation of transforming growth factor-beta 1 expression by the hepatitis B virus (HBV) X transactivator. Role in HBV pathogenesis", *J Clin Invest.*, 97(2):388-95 (1996).

Zlokarnik, et al., "Quantitation of transcription and clonal selection of single living cells with beta-lactamase as reporter", *Science*, 279(5347):84-8 (1998).

\* cited by examiner

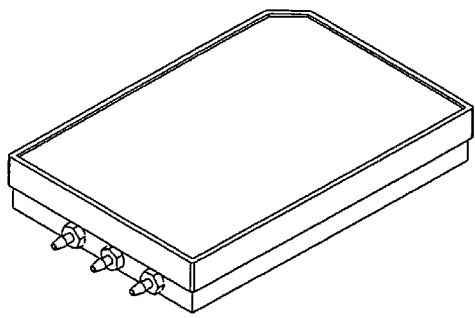
FIG. 1 ISOMETRIC VIEW (TOP)
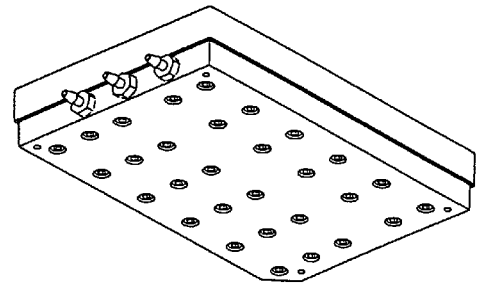
FIG. 2 ISOMETRIC VIEW (BOTTOM)
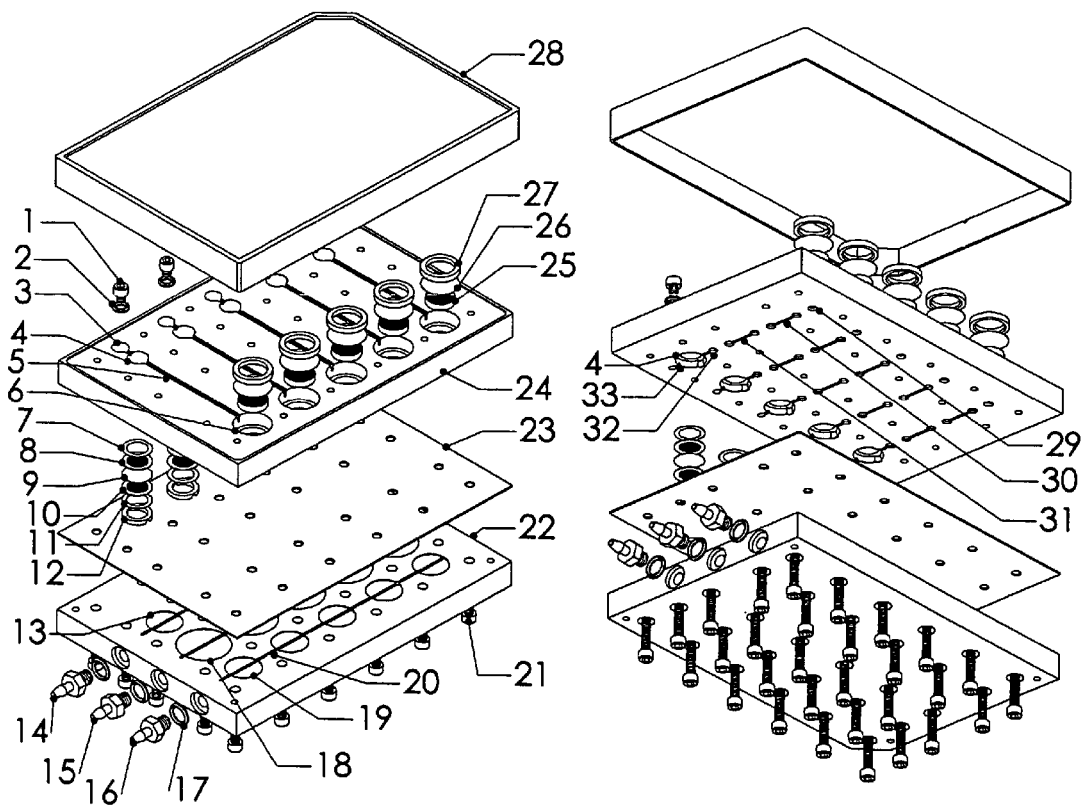
FIG. 3 EXPLODED VIEW (TOP)　　FIG 4. EXPLODED VIEW (BOTTOM)

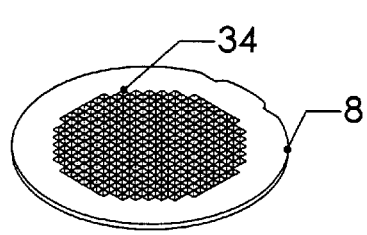
FIG. 5 ISOMETRIC DETAIL VIEW OF THE SCAFFOLD
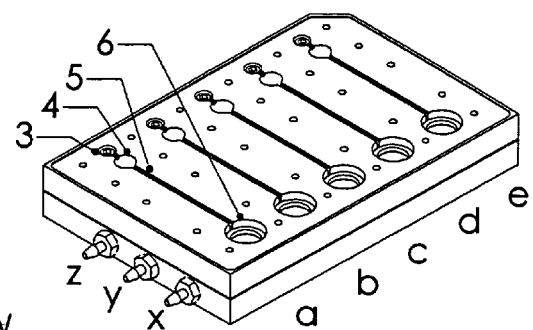
FIG. 6 ISOMETRIC VIEW (WITH THE LID REMOVED)
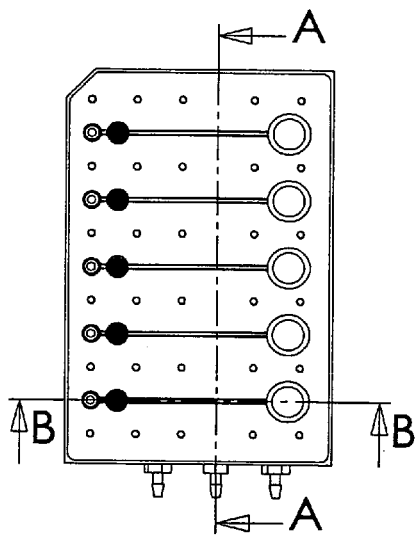
FIG. 7 TOP VIEW (WITH THE LID REMOVED)
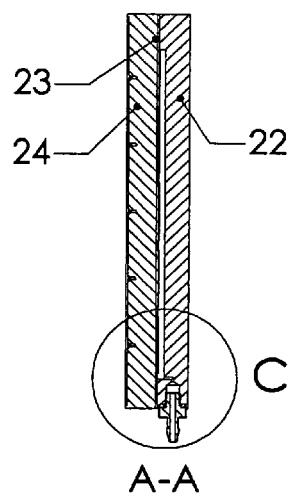
FIG. 8 CROSS-SECTION A-A
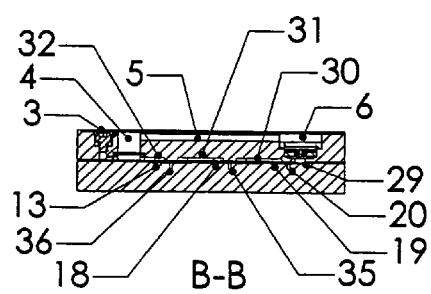
FIG. 9 CROSS-SECTION B-B
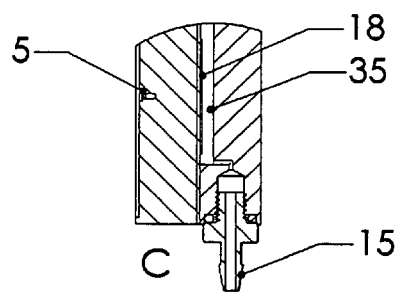
FIG. 10 DETAIL VIEW C OF CROSS-SECTION A-A

PERFUSED THREE-DIMENSIONAL CELL/TISSUE DISEASE MODELS

CROSS-REFERENCE TO RELATED APPLICATIONS

This application claims priority to U.S. Provisional Application Ser. No. 60/572,583 filed in the U.S. Patent and Trademark Office on May 19, 2004.

STATEMENT REGARDING FEDERALLY SPONSORED RESEARCH OR DEVELOPMENT

This invention was made with government support awarded by the National Institutes of Health under Grant Number 5-U19-ES011399-05. The United States government has certain rights in this invention.

BACKGROUND OF THE INVENTION

The present invention relates to an array of perfused bioreactors in a "multiwell plate" format, wherein each bioreactor of the array consists of a microscale matrix seeded with cells which forms a microtissue, multiple tissues, and/or cell aggregate and methods for using the array in high throughput assays, for example, for determining the effect of biological and/or chemical agents on the microscale tissue arrays, studying tissue-tissue interactions, or for detecting the presence of biological and/or chemical agents.

Tissue engineering has emerged as a scientific field which has the potential to aid in human therapy by producing anatomic tissues and organs for the purpose of reconstructive surgery and transplantation. It combines the scientific fields of materials science, cell and molecular biology, and medicine to yield new devices for replacement, repair, and reconstruction of tissues and structures within the body. Many approaches have been advocated over the last decade. One approach is to combine tissue specific cells with open porous polymer scaffolds which can then be implanted. Large numbers of cells can be added to the polymer device in cell culture and maintained by diffusion. After implantation, vascular ingrowth occurs, the cells remodel, and a new stable tissue is formed as the polymer degrades by hydrolysis.

A number of approaches have been described for fabricating tissue regeneration devices for either in vitro or in vivo growth of cells. Polymeric devices have been described for replacing organ function or providing structural support. Such methods have been reported by Vacanti, et al., *Arch. Surg.* 123:545-49 (1988); U.S. Pat. No. 4,060,081 to Yannas, et al.; U.S. Pat. No. 4,485,097 to Bell; and U.S. Pat. No. 4,520,821 to Schmidt, et al. In general, the methods used by Vacanti, et al., and Schmidt, et al., can be practiced by selecting and adapting existing polymer fiber compositions for implantation and seeding with cells, while the methods of Yannas and Bell produce very specific modified collagen sponge-like structures.

Tissue regeneration devices must be porous with interconnected pores to allow cell and tissue penetration, if the device is of any significant thickness. Factors such as pore size, shape, and tortuosity can all affect tissue ingrowth but are difficult to control using standard processing techniques. U.S. Pat. No. 5,518,680 to Cima & Cima describes the use of solid free form fabrication techniques, especially three dimensional printing of polymer powders, to form matrices which can be seeded with dissociated cells and implanted to form new structures. The advantages of the solid free form methods to construct specific structures from biocompatible synthetic or natural polymers, inorganic materials, or composites of inorganic materials with polymers, where the resulting structure has defined pore sizes, shapes and orientations, particularly different pore sizes and orientations within the same device, with more than one surface chemistry or texture at different specified sites within the device, is readily apparent. However, the devices still have a major limitation: ingrowth of new tissue to form blood vessels which sustain the implanted cells must occur at the right time relative to the increasing cell density within the matrix to sustain the implanted cells, and other tissues must not encapsulate or infiltrate the matrix to choke out or otherwise destroy the implanted cells.

PCT/US96/09344 to Massachusetts Institute of Technology and Childrens' Medical Center Corporation describes the use of solid free-form fabrication (SFF) methods to manufacture devices for allowing tissue regeneration and for seeding and implanting cells to form organ and structural components, which can additionally provide controlled release of bioactive agents, wherein the matrix is characterized by a network of lumens functionally equivalent to the naturally occurring vasculature of the tissue formed by the implanted cells, and which can be lined with endothelial cells and coupled to blood vessels or other ducts at the time of implantation to form a vascular or ductile network throughout the matrix.

None of this technology, however, provides a means to maintain the tissue in vitro, nor to use the tissue as a diagnostic or screening tool. Cells placed in typical in vitro culture generally lose at least some key differentiated physiological functions that they normally exhibit as part of organized tissues in the body. Thus, while cultured cells may be adequate for certain applications, for example, in detection of toxins and pathogens, they are certain to fail in other applications, for example, screening of drug which are metabolized by the tissues, or drugs which are cleared through interaction with a complex organ, not just a single isolated cell type. For example, no in vitro model of infection exists for hepatitis B virus (HBV) and hepatitis C virus (HCV), presumably because primary hepatocytes in typical culture situations rapidly stop expressing the cell surface receptors the viruses use to enter the cell. One can infer from this example of a known pathogen, which cannot currently be screened using cultured cells, that unknown pathogens (or toxins), which often utilize receptor-mediated uptake, could similarly elude detection in cultured cells. Similarly, drugs that must be bound by cell specific receptors to be taken up by the cells to be active, also cannot be tested in such systems. Xenobiotic metabolism, which is primarily carried out by a set of enzymes in the liver, is another function rapidly lost by cultured hepatocytes. Although the hepatic enzymes render most exogenous compounds less toxic, other molecules (as a common example, the pain-relieving drug acetaminophen) can actually become more toxic when metabolized by the liver. It is therefore critical to have a system for screening of drugs which can mimic in vivo conditions.

Currently, no in vitro models or animal models adequately capture the complex responses of human tissues to drugs and environmental agents. Furthermore, no in vitro model captures the complex biology of tumor cell interactions with adjacent normal tissues. Each year, many new drugs fail in early clinical trials due to unanticipated toxicity, especially liver toxicity, or due to failure to account for liver metabolism of anti-tumor agents. Liver cells rapidly lose liver-specific functions when placed in culture. Thus assessing long-term toxicity of drugs on human liver tissue in vitro is not possible. Further, sources of human liver cells are scarce, and are not able to meet the demand for cell and tissue-based assays in the pharmaceutical industry. Further, the ability to culture human tissue provides the opportunity to create models of single-cell metastasis and the very first stages of tumor growth, providing a means to culture difficult-to-culture cancer, to predict the propensity of a given tumor to metastasize and grow, to study tumor biology, and to test the efficacy of anti-cancer compounds.

The current state-of-the art 2D and 3D culture methods do not enable perfusion through the tissue mass in a manner that replicates physiological flow.

U.S. Pat. No. 6,197,575 to Griffith, et al., describes a micromatrix and a perfusion assembly suitable for seeding, attachment, and culture of complex hierarchical tissue or organ structures.

It is therefore an object of the present invention to provide an apparatus for in vitro analyses that effectively model disease in tissue and/or organs but which does not require tissue or organs.

SUMMARY OF THE INVENTION

A system has been constructed that recapitulate the features of a capillary bed through normal human tissue. The system facilitates perfusion of three-dimensional (3D) cell monocultures and heterotypic cell co-cultures at the length scale of the capillary bed. The system also allows the addition of a second cell type such as a tumor cell after the tissue has been formed. A major feature is that the system can be utilized within a "multiwell plate" format amenable to high-throughput assays compatible with the type of robotics commonly used in pharmaceutical development. The system provides a means to conduct assays for toxicology and metabolism and as a model for human diseases such as hepatic diseases, including hepatitis, exposure-related pathologies, and cancer. Cancer applications include primary liver cancer as well as metastases from other cancers, and for linking drug metabolism with anti-tumor activity. The system is particularly useful for complex and chronic diseases such as cancer, viral infection, and chronic liver fibrosis. The system can also be used as a means of testing gene therapy approaches for treating disease and inborn genetic defects.

BRIEF DESCRIPTION OF THE DRAWINGS

FIG. 1 is an isometric view (top) of an array of perfused bioreactors in multiwell plate format.

FIG. 2 is an isometric view (bottom) of an array of perfused bioreactors in multiwell plate format.

FIG. 3 is an exploded view (top) of an array of perfused bioreactors in multiwell plate format. For simplicity, only 5-unit bioreactor array is shown.

FIG. 4 is an exploded view (bottom) of an array of perfused bioreactors in multiwell plate format.

FIG. 5 is an isometric detail view of the scaffold of an array of perfused bioreactors in multiwell plate format.

FIG. 6 is an isometric view with the lid removed from an array of perfused bioreactors in multiwell plate format.

FIG. 7 is a top view with the lid removed from an array of perfused bioreactors in multiwell plate format.

FIG. 8 is a cross-section A-A of an array of perfused bioreactors in multiwell plate format.

FIG. 9 is a cross-section B-B of an array of perfused bioreactors in multiwell plate format.

FIG. 10 is a detail view C of the cross-section A-A of an array of perfused bioreactors in multiwell plate format.

DETAILED DESCRIPTION OF THE INVENTION

I. System

A system, and methods of manufacture and use thereof, have been developed based on a perfused micromatrix approach modified to utilize highly parallel means for circulating cell culture medium through the micromatrices of tissue or organ structures, making the technology exceedingly suitable for high throughput assays. This system has applications in testing drug toxicity, models of cancer metastasis, stem cell culture, and other human disease models. The system has as its basic components a dense array of perfusion bioreactor and reservoir pairs for cell or tissue culture, and valves and pumps actuated in parallel via common control channels and re-circulating medium through the array of bioreactor and reservoir pairs. Each bioreactor of the array includes a bioreactor well and its own reservoir well. The bioreactor wells and reservoir wells are connected by fluidic channels allowing re-circulation of cell culture medium. Each bioreactor/reservoir pair is fluidically isolated from all other bioreactor/reservoir pairs in the array. The valves and pumps of all bioreactors in the array are actuated in parallel via common hydraulic or pneumatic control channels.

The bioreactor/reservoir pairs are fabricated or microfabricated in the fluidic manifold. The control channels are fabricated or microfabricated in the control manifold. Diaphragm valves are created by sandwiching a monolithic elastomeric membrane between fluidic and control manifolds. The membrane between the control and fluidic channels can be deflected by hydraulic or pneumatic actuation applied through the control channels. Cell culture medium in multiple bioreactors is pumped by sequential actuation of the valves connected in series.

Each bioreactor includes a well including a three-dimensional cell/tissue support structure. In a preferred embodiment, the cell scaffold or carrier is made out of a synthetic or natural porous material. In the most preferred embodiment, the cell scaffold is formed by an array of microchannels in a solid film or sheet supported by a microporous filter or membrane. In a particularly preferred embodiment, the scaffolds can be manually or robotically ejected from the bioreactor wells. In a preferred embodiment, all bioreactors/reservoir pairs in the array are covered by a common removable lid, and cell/tissue seeding, agent addition, or sample collection can be added by pipetting or robotics.

In one embodiment, representative of systems for use herein, the array for simplicity includes only five bioreactor/reservoir pairs in the multiwell plate format as shown in FIGS. 1-10. However, the size of the components can be easily scaled-down and a considerably higher number of bioreactor/reservoir pairs can be placed on a single plate. In the current embodiment, the design of the perfused bioreactor array in the multiwell plate format has been improved by increasing the number of reactors per plate from the original five reactor prototype to a twelve reactor prototype, as well as increasing the cell capacity of each reactor. The scaffolds are now accessible from the top and the vent ports have been eliminated from the plate. The main functional component of each bioreactor is a well 4 with a 3D cell/tissue holding scaffold or carrier 8. The design has also been improved by including rims in the wells to reduce meniscus of the fluid surface and thereby minimizing the optical distortion during cell/tissue observation under a microscope; and making the reactor/reservoir pairs in the chimney arrangement to minimize cross-contamination between the adjacent reactors. The chimneys can be matched with rings of the corresponding shape in the lid to minimize evaporation of the fluid from the reactor wells, reservoir wells, and the connecting surface channels. Making the valves in the clamshell shape (normally open) compensates for a stretched or wrinkled membrane and improves the valve performance. Making the valves and pumps of an oblong shape instead of circular reduces areas where air bubbles can be trapped.

The scaffold or carrier can be made using conventional silicon processing technology, such as photolithography, wet etching, or deep reactive ion etching; micromachining; electro-discharge machining; reaction injection molding; thermoplastic injection molding; micromolding; punching; any of the solid free form technologies, such as three dimensional printing; or other types of manufacturing which can create micro through-holes in sheets of material, especially manufacturing technologies for plastics, such as micromolding, embossing, laser drilling, or electron beam machining. Molds for some of these processes can be made using methods such as lithography and micromachining, electro-discharge machining, and electroplating.

A number of materials are commonly used to form a matrix. Unless otherwise specified, the term "polymer" will be used to include any of the materials used to form the matrix, including polymers and monomers which can be polymerized or adhered to form an integral unit, as well as inorganic and organic materials, as discussed below. In one embodiment the particles are formed of a polymer which can be dissolved in an organic solvent and solidified by removal of the solvent, such as a synthetic thermoplastic polymer, either biodegradable or non-biodegradable, such as polyesters, polyurethanes, polystyrene, polycarbonates, ethylene vinyl acetate, poly(anhydrides), polyorthoesters, polymers of lactic acid and glycolic acid and other a hydroxy acids, and polyphosphazenes, protein polymers, for example, albumin or collagen, or polysaccharides. Examples of non-polymeric materials which can be used to form the matrix include organic and inorganic materials such as hydoxyapatite, calcium carbonate, buffering agents, and lactose, as well as other common excipients used in drugs, which are solidified by application of adhesive or binder rather than solvent. In the case of polymers for use in making devices for cell attachment and growth, polymers are selected based on the ability of the polymer to elicit the appropriate biological response from cells, for example, attachment, migration, proliferation and gene expression.

Other suitable polymers can be obtained by reference to The Polymer Handbook, 3rd edition (Wiley, N.Y., 1989).

For microstructures tailored to bone, inorganic powders in the final device increase the strength of the device and provide a source of minerals for the regenerating tissue. The strength requirements of soft tissues such as liver are substantially less than for bone, so greater void fractions in the final devices can be tolerated.

Referring to FIGS. 1-10, the cell/tissue support structures 8 can be formed, for example, by a porous membrane or by an array of microchannels in a solid film or sheet supported by a microporous filter 9. The porous scaffolds can be fabricated, for example, by fiber bonding (Vacanti, et al. *MRS Proceedings, vol.* 252 (1992); Mikos, et al., J. Biomed. Mater. Res. 27:183-189 (1993)), solvent casting/particulate leaching (Mikos, et al., Biomaterials 14:323-330 (1993)), gas foaming (Mooney, et al., Biomaterials 17:1417-1422 (1996)), and gas separation (Lo, et al., Tissue Engineering 1:15-28 (1995)). Silicon scaffolds with an array of microchannels can be microfabricated using appropriate technologies such as by deep reactive ion etching technique (Powers, et al., Biotechnology and Bioengineering, 78:257 (2002)). Polymer scaffolds with microchannels can be produced by laser-micromachining (Brenan, et al., Proc. SPIE, 3912, 76-87; Prog. Biomed. Optics, Micro- and Nanotechnology for Biomedical and Environmental Applications, San Jose, Jan. 26-27, 2000), injection molding (Weibezahn, et al., Micro System Technologies '94, H. Reichl and A. Heuberger, eds., vde-verlag gmbh, Berlin, pp. 873-878) or photopolymerization.

The solid scaffold 8 with microchannels can have a top layer containing an array of microchannels holding the cells. Each microchannel in the array is the functional unit of the bioreactor. Under this layer, there is a microporous membrane or a filter 9. The membrane can be a monolithic part of the cell holding scaffold or it can be e.g. thermally or ultrasonically bonded to it. The cell and/or tissue holding scaffold can be provided with sealing gaskets 7, 11, a support scaffold 10, and an insert 12. The microchannels 34 can have square or slit cross-section. The typical size of the square channels is several hundred microns. The slits can be from several hundred microns to several millimeters long. The scaffold thickness is typically several hundred microns.

Both the fluidic 24 and control 22 manifolds can be fabricated e.g. by micromechanical milling out of polymers such as polycarbonate. This can be cost effective in the small batch fabrication. In large volume fabrication, mass replication techniques such as injection molding and materials e.g. polystyrene or polycarbonate can be used. The membrane material can be e.g. polydimethylsiloxane (PDMS). The membrane 23 can be e.g. bonded to the fluidic and control manifold by plasma oxidizing the mating surfaces and immediately pressing the parts together (Duffy et al, Anal. Chem., 70, 4973-4984 (1998)). Alternatively, as shown in FIGS. 3 and 4, the membrane 23 can be sandwiched between the fluidic 24 and control 22 manifolds e.g. by means of a fastening 21 or latching mechanism providing a constant force on the membrane and holding the manifolds together.

The scaffold 8 can be e.g. press-fitted into the lower tapered section of the bioreactor well 4 in the fluidic manifold 24. The bioreactor well 4 is connected with the reservoir well 6 by two fluidic channels. The upper e.g. U-shaped channel 5 is used to return the cell culture medium from the bioreactor well 4 into the reservoir well 6. The bottom part of the reservoir can contain a face-off for inserting a microporous filter 26 with a filter support 25 secured in the reservoir well by a press-fitted insert 27 (Note: For clarity of the drawing, components 25, 26, and 27 were labeled on bioreactor/reservoir pair d and not a. Bioreactor/reservoir pairs a, b, c, d, and e in the array on the plate are identical. See FIG. 6 for labeling of bioreactor/reservoir pairs and pneumatic or hydraulic lines). The filter 26 can be used to remove cell debris from the cell culture medium. Using the filter in the reservoir well can improve reliability of the valves and pumps. In addition, it can eliminate clogging the membrane or microporous filter 9 on the backside of the cell/tissue holding scaffold 8. Filtered culture medium is sucked through port 29 into the bottom fluidic channels 30, 31, and 32 connecting the reservoir 6 and bioreactor wells 4. The channel is provided with three diaphragm valves forming a pump. The valves are created by sandwiching a monolithic elastomer membrane 23 between fluidic 24 and control 22 manifolds. A valve is created where a control channel crosses a fluidic channel. The valves can be e.g. normally closed. In that case, by applying vacuum to the channels 20, 35, and 36 (see FIG. 9) in the control manifold through the fittings 16, 15, and 14 sealed with O-rings 17, the elastomer membrane 23 is deflected down, the valves are opened, and cell culture medium fills the valve displacement chambers 19, 18, 13 and all other connected displacement chambers above the membrane 23. Applying positive pressure forces the membrane against the valve seats and the cell culture medium out of the displacement chambers of the valves. The valves of each pump are operated in a six-step cycle. Initially, all valves are closed. In the first step, the inlet valve 19 and all other valves in bioreactor/reservoir pairs b, c, d, and e connected in series by the control channel 20 are opened. In the second step, the main diaphragm valve 18 and all other valves in bioreactor/reservoir pairs b, c, d, and e connected in series by the control channel 35 are opened. In the third step, the inlet valve 19 and all other valves in bioreactor/reservoir pairs b, c, d, and e connected in series by the control channel 20 are closed. In the forth step, the outlet valve 13 and all other valves in bioreactor/reservoir pairs b, c, d, and e connected in series by the control channel 36 are opened. In the fifth step, the main diaphragm valve 18 and all other valves in bioreactor/reservoir pairs b, c, d, and e connected in series by the control channel 35 are closed. In the sixth step, the outlet valve 13 and all other valves in bioreactor/reservoir pairs b, c, d, and e connected in series by the control channel 36 are closed. The valves pumping the cell culture medium can be controlled e.g. by solenoid valves connected to sources of vacuum and pressurized air.

The normally closed monolithic membrane valves are self-priming and pump cell culture medium forward or backward simply by reversing the actuation cycle. By adjusting the volume of the diaphragm valve displacement chamber, the volume pumped per actuation can be determined at the design stage. Therefore, diaphragm pumps may be used to precisely meter the volumes of cell culture medium. If the displacement chambers of the pumps are identical, the cells/tissues in all bioreactors will be perfused at the same flow rate. In contrast, if the pumps have different volumes of displacement chambers, the cells/tissues in each bioreactor can be perfused at different flow rates.

The bioreactor and reservoir pairs are primed e.g. by manual or robotic pipetting of cell culture medium into the bioreactor or reservoir well and activating the pumping cycle in forward or reverse direction. If it is necessary to remove air bubbles from the fluidic channels, air bleeding ports 3 fitted a screw 1 and a sealing O-ring 2 can be used. The air bleeding ports are connected with the bioreactor well 5 via channel 33.

Referring to FIGS. 1-10, cells are seeded into the scaffolds 8 by dispensing (e.g. by manual or robotic pipetting) cell suspension into the bioreactor wells 4. Cell culture medium is circulated from the reservoir well 6 into the bioreactor well 4. After perfusing the 3D cell culture in the scaffold 8 in the bioreactor well 4, the cell culture medium is returned to the reservoir well 6. Each bioreactor a, b, c, d, and e (see FIG. 6) of the array has its own reservoir 6 and its microfluidic channels 5, 30, 31, and 32 are completely isolated from all other bioreactors in the array. Cell culture medium is re-circulated using diaphragm pumps. Three diaphragm valves connected in series form a diaphragm pump. The valves 19, 18, and 13 and therefore the pumps are created by sandwiching a monolithic elastomer membrane 23 between fluidic 24 and control 22 manifolds. A valve is created where a control channel crosses a fluidic channel. The thin membrane 23 between the control and fluidic channels can be deflected by hydraulic or pneumatic actuation applied through the control channels. Cell culture medium is pumped by sequential actuation of the valves connected in series. Referring to FIG. 6, the valves of all bioreactors/reservoir pairs a, b, c, d, e in the array are actuated in parallel via common hydraulic or pneumatic control lines x, y, z. As a result, in this case five completely isolated perfusion bioreactors can be addressed by three common pneumatic or hydraulic lines. However, the number of bioreactor/reservoir pairs in the array operated by three pneumatic or hydraulic lines can be considerably scaled up.

The valves and pumps are scalable and can be microfabricated in dense arrays. Unger, et al., Science 286, 113 (2000), T. Thorsen, et al., Science 298, 580 (2002), and W. H. Grover, et al., Sensors and Actuators B 89, 314 (2003), describe processes of producing monolithic valves and pumps.

Due to the fact that the array of bioreactor/reservoir pairs has an open design and is covered by a common removable lid (28), cell seeding as well as agent addition and sample collection can be performed using automated robotic workstations.

Flow rates through the system are determined by the cellular metabolic needs and by mechanical stress issues. Flow rates in the range of 0.1-1 microliter/min of medium per 1000 cells are required on a near-continuous basis (short periods of up to 15 min of no flow are feasible). Each bioreactor typically contains from 500-50,000 cells depending on the type of assay being performed. The design of the scaffold allows the system to be scaled very readily in units of ~500 cells (i.e., one channel). The flow rates through the system might be varied during the time of culture or assay in order to perform the assay (e.g., flow rates might be slowed to allow complete conversion of a compound, or increased in order to keep a constant concentration of the compound).

Sensors

Sensors can be used to detect changes in pH, oxygen levels, specific metabolites such as glucose, presence or absence of an indicator molecule such as a viral protein, or any other indicia of an effect on the tissues or a material exposed to the tissues within the bioreactor.

In one embodiment, readouts of injury or infection are based on changes in fluorescence of the tissue as detected by a miniaturized fiber optic array which excites fluorescence via either single or multiphoton means. The nature of the excitation is a critical parameter addressed in the technology development. Multiphoton excitation offers several advantages over single photon, in terms of resolution and prevention of tissue damage.

Many types of fluorescent readouts are possible. Changes in basic metabolic parameters of the tissue can be assessed by measuring the change in NAD(P)H levels via intrinsic fluorescence of these molecules. Cells can also be pre-loaded with a dye which leaks in the case of membrane damage, resulting in a decrease of fluorescent intensity. Alternatively or in addition, reporter genes can be transfected into the cells under the control of a stress-related promoter which is activated during tissue injury to produce a fluorescent product. This latter approach is of particular interest for detecting viral infection on a rapid time scale.

The objective in the detection scheme is to provide a fast, sensitive, field-adaptable, and minimally invasive fluorescence spectroscopic readout of tissue injury. A panel of potential indicators which will vary in either fluorescence intensity and/or spectrum have been identified. Since responses may require monitoring cellular biochemical state within normal tissue structure, it may not be sufficient to analyze only the surface layer of cells in the tissue, but to selectively monitor the cellular strata several cells deep into the channel interior. These requirements can be summarized into four design criteria for the optical detection system: (1) depth selection detection in thick (300 μm) tissue, (2) flexible excitation and detection scheme to image a variety of indicators, (3) minimally invasive to the living tissue culture in the device, (4) fast signal detection with high sensitivity, (5) rugged and field adaptable.

Using single photon excitation, confocal detection is needed to separate fluorescence which originates from the channel interior from its surface. A confocal microscope is a well-developed instrument designed to optically section thick specimens. Two apertures or pinholes are arranged in conjugate planes; one in front of the light source and one in front of the detector. This design can be simplified and made more robust for on-line detection by the use of single mode fiber optics. Through a dichroic beam splitter, excitation light is introduced into a single mode fiber (FIG. 1; beam splitter is not depicted). The light emitted from the fiber can be collimated by a lens. A second lens can focus the collimated light into the channel of the tissue chip. High resolution is not critical in this application no imaging is required—and thus low optics and the chip to provide spaces for the hydraulic design in the flow chamber. The fluorescence from the sample is collected by two relay lenses and reflected back into the single mode fiber. The small diameter fiber functions simultaneously as the excitation and emission pinhole aperture in this system. Fluorescence originated outside the focal region can not be refocused by the relay lenses on to the fiber optics and is rejected. This process provides us depth discrimination. A number of chromophores with excitation wavelengths spanning near-UV to the blue-green region of the spectra can be considered during this project. Fluorescence indicators of particular interest are the endogenous chromophores, pyridine nucleotides. The pyridine nucleotides, NAD(P)H are excited in the region 365 nm and fluoresce in the region 400-500 nm. Another indicator of interest is green fluorescence protein (GFP) which can be excited in either near UV or the blue region of the spectrum and typically emits at about 510 nm. In order to excite this wide range of chromophores, a tunable UV argon-ion laser can be acquired for this study. Although this laser is not sufficiently robust for field application, it provides the flexibility to test a large set of fluorophores. After the proper set of chromophores is identified, less flexible but more robust and compact laser system can be easily incorporated. This fiber optic confocal design is a mature technology and can be rapidly incorporated into the tissue sensor to assess the changes in cellular biochemistry under toxin stress inside the tissue chip.

Although a toxin sensitive tissue chip may be built based on one-photon confocal approach, the use of two-photon approach can improve the system by increasing fluorescence signal to noise ratio and decreasing tissue damage. This new approach to study is based on two-photon microscopy developed by Denk et al. (Denk, et al., *Science* 248:73-77 (1990)). Chromophores can be excited by the simultaneous absorption of two photons each having half the energy needed for the excitation transition. Since the two-photon excitation occurs only at the focal point of a high numerical aperture objective, a region of high temporal and spatial concentration of photons. Using two-photon excitation, over 80% of the total fluorescence intensity comes from a 1 μm thick region about the focal point for a 1.25 numerical aperture objective. This depth discrimination effect of two-photon excitation arises from the quadratic dependence of two-photon fluorescence intensity upon the excitation photon flax which decreases rapidly away from the focal plane. The depth discrimination is a result of the physics of the excitation method and no confocal detection pinhole aperture is needed. This localization of two-photon excitation can be best visualized in a simple bleaching experiment.

To demonstrate the effect of two photon excitation, a two photon excitation volume was focused in the center of a 15 μm fluorescent latex sphere. The excitation volume was scanned repeatedly along the x axis until photobleaching occurred. A 3-D image stack of the latex sphere was acquired, in which a series of images are x-y planes of the sphere at increasing distance from the center. No photobleaching was observed beyond 1 μm.

Two-photon excitation allows selective assessment of the tissue physiological state at any point in the interior of the tissue chip channel. There are a number of advantages to the multi-photon approach as compared with confocal approach where the sample's absorption and scattering coefficients are high, such as those in tissues: (1) The typical scattering and absorption in the infrared spectral range is over an order of magnitude less than the near UV or the blue-green region. Using infrared excitation in the two-photon microscope minimizes the attenuation of the excitation signal. (2) Confocal microscopy uses the emission pinhole aperture to reject out of focus light. Inside deep tissue, scattering of the signal photons is inevitable. The consequent path deviation results in a significant loss of these photons at the confocal pinhole. The collection geometry for the fluorescence photons is less critical in the two-photon case where a large area detector can be used without a pinhole aperture. Most of the forward-scattered photons can be retained. (3) Two-photon excitation minimizes tissue photo-damage. Conventional confocal techniques obtain 3-D resolution by limiting the observation volume, but fluorescence excitation occurs throughout the hour-glass-shaped light path. In contrast, two-photon excitation limits the region of photo-interaction to a sub-femtoliter volume at the focal point. (4) Two-photon excitation wavelengths are typically red-shifted to about twice the one-photon excitation wavelengths. This wide separation between excitation and emission spectrum ensures that the excitation light and the Raman scattering can be rejected while filtering out a minimum of fluorescence photons. (5) Many fluorophores have found to have very broad two-photon absorption spectra. A single properly-chosen excitation wavelength can excite a wide range of fluorophores with emission bands ranging from near-UV to near-infrared.

These advantages of the two-photon approach make it an attractive alternative to single photon approach. However, the miniaturization of a two-photon system still requires extensive research. Problems such as pulse dispersion in fiber system still have to be resolved. Therefore, a second focus of developing optical system for the tissue chip is the development of miniaturization technology for two-photon excitation spectroscopy. Two-photon microscopes can be constructed to assess tissue toxin response as a function of tissue depth in the chip channel and to optimize the optics configuration to maximize detection efficiency in the unique geometry of the tissue chip. If the two-photon approach can be shown to be advantageous as compared with that of the one-photon confocal method, a final miniaturized fluorescence detection system based on two-photon excitation can be constructed.

Miniaturized fiber optic fluorescence spectrometers are available which can be used. One system is based on an one-photon excitation and confocal detection scheme. A second system involves the use of two-photon excitation. The advantage of this system includes lower tissue damage, higher throughput and higher versatility in terms simultaneous monitoring of multiple indicators.

Sensors other than fluorescent sensors can also be used. For example, samples can be analyzed by using infrared spectrophotometers, ultraviolet spectrophotometers, gas chromatograms, high performance liquid chromatograms, mass spectrometry, and other detection means known to those of skill in the art. These can be used to measure nutrients, gases, metabolites, pH, and other indicators of cell activity, infection, and metabolism. Measurements may be made on the cells themselves or on the culture medium, or both. Measurements may be made as a time course assay or an end-point assay or both during culture and at the end of culture.

II. Applications

The technology is amenable to large-scale integration. This makes performing massively parallel assays possible. For example, different cells or cell mixtures can be seeded into each bioreactor well. Alternatively, different cell culture medium can be circulated through every bioreactor/reservoir pair or the cells/tissue in each bioreactor well can be exposed to a different agent. An initial cell type can be added (e.g., human liver cell isolates), stabilized into tissue, and then a second cell type (e.g., cancer cell) added to examine the response.

The type(s) of cells determine the function of the tissue. As used herein, tissue refers to an aggregation of cells more or less similar morphologically and functionally. In one embodiment, the matrix is seeded with a mixture of cells including endothelial cells and at least one type of parenchymal cells, such as hepatocytes, pancreatic cells, or other organ cells, or the matrix is seeded with totipotent/pluripotent stems cells which can differentiate into cells, including endothelial cells to form a cells. Mixtures of cells of diverse function are referred to as cellss. Endothelial cells (and in some cases other cells such as pericytes or stellate cells) can form "blood vessels" throughout the tissue. An organ refers to a differentiated structure of an organism composed of various cells or tissues and adapted for a specific function (*McGraw-Hill Dictionary of Bioscience*).

In the preferred embodiment, donor tissue is dissociated into individual cells, the cell types separated and purified, and recombined within the channels in a way which allows the histotypic architecture of the tissues to reform. Standard procedures are used to obtain and dissociate cells. For example, primary rat hepatocytes and non-parenchymal cells can be isolated using standard collagenase perfusion (Griffith, et al., *Ann. N.Y. Acad. Sci.* 831 (1997); Cima, et al., *Biotech. Bioeng.* 38:145-58 (1991)). Human hepatocytes can be obtained from collagenase perfusion of tissue obtained from liver resections or from liver biopsies through the New England Organ Bank (Fontaine, et al., *J. Ped. Surg.* 30:56-60 (1995)). Rat microvascular endothelial cells can be obtained from collagenase perfusion of fat. Human microvascular endothelial cells can be obtained from Clonetics. It is unlikely that matching of tissue types for microvascular endothelium is required, as endothelium exhibits great plasticity to adapt to new environments. Embryonic stem cells (ES cells) can be cultured in the totipotent state using standard techniques with differentiation induction, for example, by replacing LIF with various cytokines.

A variety of different cells can be applied to the support matrices. In the preferred embodiments, these are normal human cells or human tumor cells. The cells may be a homogeneous suspension or a mixture of cell types. The different cell types may be seeded onto and/or into the matrices sequentially, together, or after an initial suspension is allowed to attach and proliferate (for example, endothelial cells, followed by liver cells). Cells are seeded into the scaffolds by dispensing (e.g. by manual or robotic pipetting) cell suspension into the bioreactor wells. To allow the cells to attach to the scaffolds, the perfusion flow can be reduced or turned off for a period of time immediately after the seeding.

Culture medium composition must be considered from two perspectives: basic nutrients (sugars, amino acids) and growth factors/cytokines. Co-culture of cells often allows reduction or elimination of serum from the medium due to production of regulatory macromolecules by the cells themselves. The ability to supply such macromolecular regulatory factors in a physiological way is a primary reason 3D perfused co-cultures are used. A serum-free medium supplemented with several growth factors suitable for long-term culture of primary differentiated hepatocytes (Block, et al., *J. Cell Biol.* 132:1133-49 (1996)) has been tested and found to support co-culture of hepatocytes with endothelial cells. ES cells are routinely maintained in a totipotent state in the presence of leukemia inhibitory factor (LIF) (Williams, et al., *Nature* 336:684-87 (1988)), which activates gp130 signaling pathways (Saito, et al., *J. Immunol.* 148:4066-71 (1992)). Several medium formulations can support differentiation of ES cells, with different cytokine mixes producing distinct patterns of differentiation (Millauer, et al., *Cell* 72:835-46 (1993); Gendron, et al., *Dev. Biol.* 177:332-46 (1996); Bain, et al., *Dev. Biol.* 168:342-57 (1995)). Medium replacement rates will be determined by measuring rates of depletion of key sugars and amino acids as well as key growth factors/cytokines. Growth factor depletion is a seldom-recognized limiting factor determining medium replacement rates (Reddy, et. al., *Biotechnol. Prog.* 10:377-84 (1994)). If cell culture medium with sodium bicarbonate is used, the environmental control can be provided by e.g. placing the module with bioreactor/reservoir pairs into a $CO_2$ incubator. Reagent addition or sample extraction should be in that case performed in a sterile environment. If cell culture medium with an organic buffer is used, the module with bioreactor/reservoir pairs can be placed in a sterile environment where manual or robotic reagent addition or sample extraction can be performed.

Cells can be obtained from cell culture or biopsy. Cells can be of one or more types, either differentiated cells, such as endothelial cells or parenchymal cells, including nerve cells, or undifferentiated cells, such as stem cells or embryonic cells. In one embodiment, the matrix is seeded with a mixture of cells including endothelial cells, or with totipotent/pluripotent stem cells which can differentiate into cells including endothelial cells, which will form "blood vessels", and at least one type of parenchymal cells, such as hepatocytes, pancreatic cells, or other organ cells.

Cells can be cultured initially and then used for screening of compounds for toxicity, where different reactors contain different cell types (for example, liver in reactors 1-10, pancreatic cells in reactors 11-20, skin cells in reactors 21-30, etc). Cells can also be used for screening of compounds having a desired effect. For example endothelial cells can be used to screen compounds which inhibit angiogenesis. Tumor cells can be used to screen compounds for anti-tumor activity. Cells expressing certain ligands or receptors can be used to screen for compounds binding to the ligands or activating the receptors. Stem cells can be seeded, alone or with other types of cells. Cells can be seeded initially, then a second set of cells introduced after the initial bioreactor tissue is established, for example, tumor cells that grow in the environment of liver tissue. The tumor cells can be studied for tumor cell behaviors or molecular events can be visualized during tumor cell growth. Cells can be modified prior to or subsequent to introduction into the apparatus. Cells can be primary tumor cells from patients for diagnostic and prognostic testing. The tumor cells can be assessed for sensitivity to an agent or gene therapy. Tumor cell sensitivity to an agent or gene therapy can be linked to liver metabolism of set agent or gene therapy. Cells can be stem or progenitor cells and the stem or progenitor cells be induced to differentiate by the mature tissue.

Mature cells can be induced to replicate by manipulation of the flow rates or medium components in the system.

The system has many different applications: identification of markers of disease; assessing efficacy of anti-cancer therapeutics; testing gene therapy vectors; drug development; screening; studies of cells, especially stem cells; studies on biotransformation, clearance, metabolism, and activation of xenobiotics; studies on bioavailability and transport of chemical agents across epithelial layers; studies on bioavailability and transport of biological agents across epithelial layers; studies on transport of biological or chemical agents across the blood-brain barrier; studies on acute basal toxicity of chemical agents; studies on acute local or acute organ-specific toxicity of chemical agents; studies on chronic basal toxicity of chemical agents; studies on chronic local or chronic organ-specific toxicity of chemical agents; studies on teratinogenicity of chemical agents; studies on genotoxicity, carcinogenicity, and mutagenicity of chemical agents; detection of infectious biological agents and biological weapons; detection of harmful chemical agents and chemical weapons; studies on infectious diseases; studies on the efficacy of chemical agents to treat disease; studies on the efficacy of biological agents to treat disease; studies on the optimal dose range of agents to treat disease; prediction of the response of organs in vivo to biological agents; prediction of the pharmacokinetics of chemical or biological agents; prediction of the pharmacodynamics of chemical or biological agents; studies concerning the impact of genetic content on response to agents; filter or porous material below microscale tissue may be chosen or constructed so as bind denatured, single-stranded DNA; studies on gene transcription in response to chemical or biological agents; studies on protein expression in response to chemical or biological agents; studies on changes in metabolism in response to chemical or biological agents; prediction of agent impact through database systems and associated models; prediction of agent impact through expert systems; and prediction of agent impact through structure-based models.

The bioreactors can be modified by attachment of ligands or specific receptor binding molecules to modify attachment or behavior of the cells.

Drugs can be added and circulated through the tissue mass in each individual bioreactor, with samples taken at several time points to determine metabolic clearance profiles; a dose-response can be determined by using drug dilutions in several individual reactors on a single plate. Different doses of drugs can be added to different bioreactors within the same plate and incubated for days or even weeks to determine chronic and subchronic toxicity responses. The ultimate readout is compatible with optical plate assays. The system can also be used to screen on the cells, for an effect of the cells on the materials (for example, in a manner equivalent to tissue metabolism of a drug).

If it is desirable to investigate the biological samples outside the bioreactor array (for example after performing an assay), the scaffolds with cells/tissue can be ejected from the bioreactor wells into a plate with transfer wells. This can be performed manually or robotically on all or only selected bioreactor wells.

The results from these studies can be entered into mathematical models to predict the response of organs in vivo. The results can also be entered into mathematical models to predict pharmacokinetics and/or pharmacodynamics of chemical and biological agents. The system can be integrated with other test systems, such as those which concern genomics, gene transcription, protein expression, and other biological phenomena of interest.

Test systems using microscale tissue arrays have a broad range of uses for in vitro assays. Using the arrays, one can study biotransformation, clearance, metabolism, and activation of xenobiotics. The bioavailability and transport of chemical and biological agents across epithelial layers and across the blood-brain barrier can be studied. The acute basal toxicity, acute local toxicity or acute organ-specific toxicity, teratogenicity, genotoxicity, carcinogenicity, and mutagenicity, of chemical agents can also be studied. Infectious biological agents, biological weapons, harmful chemical agents and chemical weapons can be detected. Infectious diseases and the efficacy of chemical and biological agents to treat these diseases, as well as optimal dosage ranges for these agents, can be studied. The response of organs in vivo to chemical and biological agents, and the pharmacokinetics and pharmacodynamics of these agents can be predicted. The impact of genetic content on response to the agents can be studied.

The amount of protein expression in response to chemical or biological agents can be determined. Changes in metabolism in response to chemical or biological agents can be studied. The impact of agents can be predicted through database systems and associated models, expert systems or structure-based models.

Toxic substances, including compounds that are intrinsically toxic to all cells (e.g., cyanide) and those that are metabolically converted to toxic metabolites (usually electrophiles) by parenchymal cells, can also be detected using a comprehensive approach to detect an event that will lead to cell death. This can be general and not specific; i.e., not specific for an individual toxin, but general for the entire class. Examples include mitochondrial poisons, DNA-damaging agents, and membrane-damaging agents.

Metabolite detection may be achieved by monitoring the fluid effluent from the cells using in-line detection methods such as UV, visible, or fluorescence detectors and/or mass spectrometry. In addition, the effluent from cells can be sampled periodically and analyzed for the presence of metabolites in an off-line fashion using standard analytical techniques.

The filter or porous material below the cells may be designed to incorporate trapping agents and/or substrates as a method for detecting metabolites. These trapping agents (i.e. peptides or nucleophilic organic species) would be exposed to the fluid emanating from the cells and would covalently bond to reactive metabolites generated by the cells and released into the perfusate. The complex formed by covalent linkage of the trapping agent and the reactive metabolite could then be detected in-situ or could be released from the filter or porous material by cleavage of a labile bond connecting the trapping agent to the filter or porous material. This labile bond could be cleaved by chemical means, the activity or an enzyme, or by the exposure of specific wavelengths of light.

Three potential fluorescent readouts of infection, each as a function of the time course, are cytosolic enzyme leakage, cytosofic NAD(P)H reduction, and expression of GFP linked to stress-inducible promoters in either endothelial cells or hepatocytes.

Biological toxins act by different mechanisms and may exhibit different sensitivities and time courses of actions compared to chemical toxins. Biological toxins can be evaluated for their effects on both liver and ES cells. Representative examples include Shiga-like toxin (SLT or verotoxin), produced by Enterohemorrhagic *Escherichia coli* (EHEC), and Vac (vacuolating toxin), produced by *Helicobacter pylori*. SLT stops host cell protein synthesis by inactivating the 60S subunit of host cell ribosomes (Tesh, et al., *Mol. Microbiol.* 5:1817-22 (1991)). Vac toxin binds to cells through an unknown receptor, and induces vacuole formation, probably by inhibiting sodium-potassium ATPase activity.

The technical challenges associated with monitoring cytotoxicity in real time within the context of this dynamic tissue sensor can be met using a variety of Laser Induced Fluorescence (LIF) techniques. LIF provides detection limits in the low femtomoles ($10^{-15}$ moles), and for ideal analytes, attomole ($10^{-18}$ moles) detection limits are possible. Two primary endpoints have been identified for monitoring the effects of toxic insult to the tissue sensor: decrease in NAD(P)H levels within the cells and a loss of cellular membrane integrity.

A decrease in intracellular NAD(P)H in response to toxin exposure is observed in the case of mitochondrial poisons (e.g., menadione or cyanide) due to disruption of the respiratory chain. Intracellular NADH and NAD(P)H levels are also depleted in response to nuclear toxins (e.g., nitrogen mustards) via the process of poly ADP-ribosylation of proteins associated with DNA. The cellular pool of NAD(P)H can be monitored by in-situ fluorescence spectroscopy as described above for fluctuations in response to toxin or pro-toxin exposure.

A loss of membrane integrity is a common endpoint for all cytotoxic pathways (i.e., necrosis or apoptosis) and can be observed after all cytolethal exposures to the tissue-based sensor. The loss of membrane integrity is accompanied by a leakage of intracellular constituents into the perfusate. One approach to capitalize on this loss of membrane integrity can be to load the cells of the bio-sensor with poly-esterified derivatives of fluorescein (e.g., Calcein AM, Abs: 494 Em: 517). These non-fluorescent derivatives passively enter the cells after which esterases hydrolyze them to poly-anionic fluorescent dyes that are retained in the cells. An increase in cell membrane permeability due to a toxic insult can lead to loss of dye to the perfusate. Thus, monitoring a decrease in fluorescence of the dye retained by the cells can provide a readout of cytotoxicity.

Another approach to quantify cytotoxicity by loss of membrane integrity can be to observe an increase in enzymatic activity (e.g., alkaline phosphatase and γ-glutamyl transpeptidase) released into the perfusate. This can be accomplished through LIF spectroscopy of an in-line enzyme detector consisting of immobilized pro-fluorophore or pro-chromophore enzyme substrates.

For example, this approach could be used to monitor γ-glutamyl transpeptidase activity released into the perfusate by cells array after toxic insult. A rhodamine derivative has been designed that is non-fluorescent until the action of γ-glutamyl transpeptidase liberates the free amine. The resulting product is highly fluorescent (Abs: 492 Em: 529) and remains bound to the solid support. The use of an in-line immobilized substrate allows for monitoring a cumulative signal and dramatically improves the sensitivity, as compared to detecting the signal from a soluble fluorophore circulating in the perfusate. A similar strategy can be employed to monitor alkaline phosphatase activity using an immobilized fluorescein diphosphate derivative.

One configuration of in-line detector involves immobilizing the pro-fluorophore and/or pro-chromophore enzyme substrate(s) onto the filter or porous material situated below each cells. to react to specific cellular responses emanating from each cells. Such a filter array can be designed to include substrates that respond with varying sensitivities to the same cellular response and substrates that respond to different cellular responses. In addition, redundancy (i.e., the same pro-fluorophore/chromophore present under more than one cells within an array) can be distributed throughout the cells array.

The pro-fluorophores/chromophores are designed to respond to numerous cellular responses including but not limited to enzyme leakage from the cells, fluctuations in effluent pH, and release of reactive oxygen species.

The fluorescence signal produced by each filter or porous material is proportionate to the extent of the cellular response. The array of filters or porous materials would demonstrate a characteristic fluorescence intensity pattern that would be indicative of the status of the cells array. The fluorescence signal from the array can be collected on a periodic basis as necessary using the instrumentation outlined above in the section describing sensors. The data obtained from the array of fluorophores can be interpreted by pattern recognition software to correlate the fluorescence signal pattern to the status of the cells array. Three potential fluorescent readouts of infection, each as a function of the time course, are cytosolic enzyme leakage, cytosolic NAD(P)H reduction, and expression of GFP linked to stress-inducible promoters in either endothelial cells or hepatocytes. Other flourescent readouts include activation of caspases and mitochondrial activity as reported by markers such as rhodamine 123.

We claim:

1. An apparatus comprising an array of isolated perfusion bioreactor and reservoir pairs for culturing cells or tissues, the apparatus comprising
a fluidic manifold comprising an array of fluidically isolated perfusion bioreactor and reservoir pairs for cell or tissue culture, and
a control manifold comprising common control channels actuated in parallel to simultaneously act on each pair of bioreactors and reservoirs and means for controlling timing, flow rate and volume of cell culture medium to each bioreactor and reservoir pair,
wherein each fluidically isolated perfusion bioreactor and reservoir pair is connected by a fluidic channel allowing re-circulation of cell culture medium,
wherein each perfusion bioreactor and reservoir pair is fluidically isolated from all other perfusion and bioreactor pairs,
wherein each control channel is separated from the fluidic channel by a diaphragm valve which can be deflected into a valve displacement chamber by hydraulic or pneumatic actuation,
wherein the volume of the cell culture medium pumped through the fluidic channel into either the bioreactor or the reservoir is determined by the volume of the valve displacement chamber, and
wherein each perfusion bioreactor comprises a removable three-dimensional cell or tissue support structure through which the cell culture medium is perfused.

2. The apparatus of claim 1 further comprising a pump.

3. The apparatus of claim 2 wherein the pump is an adjustable volume pump.

4. The apparatus of claim 1 wherein the bioreactor and reservoir pairs, scaffolds or channels are formed by a method selected from the group consisting of photolithography, wet etching, deep reactive ion etching, micromachining, electro-discharge machining, reaction injection molding, thermoplastic injection molding, micromolding, punching, solid free form technologies, micromolding, embossing, laser drilling, and electron beam machining.

5. The apparatus of claim 1 wherein the three-dimensional cell/tissue support structure is made out of porous material.

6. The apparatus of claim 1 wherein the cell/tissue support structure is formed by an array of microchannels in a solid film or sheet supported by a microporous filter or membrane.

7. The apparatus of claim 1 wherein all bioreactors/reservoir pairs in the array are covered by a common removable lid.

8. The apparatus of claim 1 comprising a device for manual or robotic pipetting of cell/tissue seeding, agent addition, or sample collection.

9. The apparatus of claim 1 wherein the bioreactor/reservoir pairs are fabricated or microfabricated in the fluidic manifold.

10. The apparatus of claim 1 wherein the control channels are fabricated or microfabricated in the control manifold.

11. The apparatus of claim 1 comprising diaphragm valves created by sandwiching a monolithic elastomeric membrane between the fluidic and control manifolds.

12. The apparatus of claim 1 wherein cell culture medium in multiple bioreactors is pumped by sequential actuation of the valves connected in series.

13. The apparatus of claim 1 further comprising a first set of cells.

14. The apparatus of claim 13 further comprising a second set of cells introduced after the initial bioreactor tissue is established.

15. The apparatus of claim 14 wherein the second set of cells are tumor cells.

16. The apparatus of claim 14 where the second set of cells are stem cells.

17. The apparatus of claim 13 comprising tumor cells that grow in the environment of liver tissue.

18. The apparatus of claim 13 comprising tumor cells that can be studied for tumor cell behaviors.

19. The apparatus of claim 14 wherein molecular events can be visualized during tumor cell growth.

20. The apparatus of claim 1 wherein the first set of cells can be modified prior to or subsequent to introduction into the apparatus.

21. The apparatus of claim 1 comprising primary tumor cells from patients for diagnostic and prognostic testing.

22. The apparatus of claim 21 wherein the tumor cells can be assessed for sensitivity to an agent or gene therapy.

23. The apparatus of claim 17 wherein tumor cell sensitivity to an agent or gene therapy is linked to liver metabolism of set agent or gene therapy.

24. The apparatus of claim 16 wherein the second set of cells introduced are stem or progenitor cells and the stem or progenitor cells are induced to differentiate by the mature tissue.

25. The apparatus of claim 13 comprising mature cells inducible to replicate by manipulation of the flow rates or medium components in the system.

* * * * *

UNITED STATES PATENT AND TRADEMARK OFFICE
CERTIFICATE OF CORRECTION

| | |
|---|---|
| PATENT NO. | : 8,318,479 B2 |
| APPLICATION NO. | : 11/133092 |
| DATED | : November 27, 2012 |
| INVENTOR(S) | : Domansky et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1010 days.

Signed and Sealed this
Twenty-first Day of October, 2014

Michelle K. Lee
*Deputy Director of the United States Patent and Trademark Office*